United States Patent [19]
Douglas

[11] Patent Number: 5,662,711
[45] Date of Patent: Sep. 2, 1997

[54] FLOW ADJUSTABLE ARTERY SHUNT

[76] Inventor: William Douglas, 18401 Newell Rd., Shaker Heights, Ohio 44122

[21] Appl. No.: 477,184

[22] Filed: Jun. 7, 1995

[51] Int. Cl.$^6$ .................................................. A61F 2/04
[52] U.S. Cl. .................................................. 623/12; 604/9
[58] Field of Search .......................... 604/8, 9; 623/3, 623/12, 1

[56] References Cited

U.S. PATENT DOCUMENTS

| | | | |
|---|---|---|---|
| 4,195,623 | 4/1980 | Zeff et al. | 604/9 |
| 4,302,854 | 12/1981 | Runge . | |
| 4,552,552 | 11/1985 | Poleschegg et al. | 604/9 |
| 4,553,956 | 11/1985 | Muller | 604/9 |
| 4,938,766 | 7/1990 | Jarvik | 623/3 |
| 4,995,857 | 2/1991 | Arnold | 623/3 |
| 5,192,310 | 3/1993 | Herweck et al. | 623/12 |
| 5,267,940 | 12/1993 | Moulder | 623/3 |
| 5,411,550 | 5/1995 | Herweck et al. | 623/12 |
| 5,411,551 | 5/1995 | Winston et al. | 623/12 |
| 5,437,601 | 8/1995 | Runge | 623/3 |

*Primary Examiner*—Michael J. Milano
*Attorney, Agent, or Firm*—Watts, Hoffmann, Fisher & Heinke

[57] ABSTRACT

An apparatus and method for treating congenital heart defects, such as cyanotic heart defects which includes a shunt implanted within a patient's cavity for communicating blood from the patient's arterial system to the patient's pulmonary system. An adjustable flow restrictor forms part of the shunt and is operative to adjust the effect of cross-section of the shunt thereby varying the blood flow rate in the shunt. An oximeter monitors the oxygen saturation levels in the blood and in cooperation with a restrictor control varies inflation of the bladder to maintain an oxygen saturation level in the blood between predetermined limits.

27 Claims, 2 Drawing Sheets

FLOW ADJUSTABLE ARTERY SHUNT

TECHNICAL FIELD

The present invention relates generally to methods and apparatus for treating a diseased human heart and, in particular, to a method and apparatus for controlling the rate of blood flow through a systemic-pulmonary shunt.

BACKGROUND ART

Because many congenital heart defects cannot be corrected entirely at birth, palliative heart surgery is performed in order to extend the life of an infant until such time that corrective heart surgery can be performed. "Cyanotic defects" is one of the categories of congenital heart defects for which palliative surgery is normally performed. A cyanotic defect is one in which malformations within the heart reduce pulmonary blood flow resulting in low oxygen saturation levels within the blood. This defect often causes a bluish hue in the patients due to the low arterial oxygen saturation levels. In many cases, children born with cyanotic congenital heart disease cannot have the defect repaired at birth, but must wait for at least one year before corrective surgery, such as a Fontan procedure can be performed.

Palliative surgery, however, is usually performed immediately on the infant in order to at least partially alleviate the low oxygen saturation level. For example, for certain cyanotic congenital heart diseases, such as tricuspid atresia, a systemic-pulmonary artery shunt is installed in order to provide a means for conveying blood from the aorta to the pulmonary system where the blood is oxygenated by the patient's lungs. Palliative surgery for non-cyanotic heart defects, such as a "Norwood" procedure for hypoplastic left heart syndrome, may use a systemic-pulmonary shunt as part of the repair.

Most shunts currently used in treating cyanotic heart disease consist of simply prosthetic tubes made from Gore-Tex®. It is believed that the pulmonary blood flow through a shunt must be maintained within certain limits to avoid adverse side effects. Excessive pulmonary blood flow may increase pulmonary vascular resistance, may burden the ventricle with volume overload, and may ultimately decrease the chance for a successful Fontan procedure later. Insufficient pulmonary blood flow will result in low oxygen saturation levels in the blood.

Attempts have been made to indirectly control the flow rate of blood through a systemic-pulmonary shunt. These attempts have traditionally utilized systemic vasoconstrictors or vasodilitators. Systemic vasoconstrictor will force more blood through the shunt; systemic vasodilitators will have the opposite effect. One recent attempt included use of $CO_2$ in the inspired gas of the patient in the immediate post-operative period. Decrease partial pressure of $CO_2$ in the arterial blood results in decreased pulmonary vascular resistance. Varying the concentration of $CO_2$ in the inspired gas allows one to vary the pulmonary vascular resistance and therefore, exert some control over the pulmonary systemic blood flow ratio.

The above methods imprecisely control the systemic pulmonary blood flow ratio and have other hemodynamic side effects. These methods are also only applicable in the intensive care unit setting. While they may help in the early post-operative period, they do not offer any control of shunt flow from the time of leaving the intensive care unit until the time of a Fontan or hemi-Fontan procedure. It is hypothesized that precise control of blood flow through the shunt from the time of palliation until the Fontan or hemi-Fontan procedure can be performed, is desirable to ameliorate the side effects of increased pulmonary vascular resistance and volume overload of the ventricle.

DISCLOSURE OF THE INVENTION

The present invention provides an improved method and apparatus for controlling the blood flow rate through a systemic-pulmonary shunt in order to maintain a balance between the arterial flow and the pulmonary flow in the patient.

According to the invention, a systemic-pulmonary shunt is implanted in the patient's chest cavity and is used to provide a fluid path from the aorta (or other systemic blood vessel) to the right, left, or main pulmonary artery. An adjustable flow control device, such as a fluid resistor forms part of the shunt and is used to adjust the flow rate of blood through the shunt. An oxygen sensor senses the oxygen saturation level of the blood in the shunt and is coupled to a controller which is preferably implanted within the patient. Signals from the oxygen sensor are used by the controller to adjust the flow control device within the shunt in order to adjust the flow rate of blood through the shunt. Since the shunt is feeding blood to the pulmonary system, the rate of blood flow through the shunt will determine the overall oxygen saturation level of the blood in the patient. Preferably, power for the controller, the oxygen sensor and the flow control device are provided by an implanted power source.

In the preferred and illustrated embodiment, the flow control device includes a bladder-like member mounted within the shunt which is inflated and deflated in order to vary the effective cross-section of the shunt. In a more preferred embodiment, the bladder is attached to a portion of the inside wall of the shunt and would conform to the wall when not inflated to provide a minimal restriction to blood flow and may be inflated to provide a substantial restriction to blood flow by blocking more than 50% of the shunt cross-section.

The oxygen sensor in the preferred embodiment is an oximeter which pierces the shunt wall in order to be in contact with blood flow in the shunt. Conventional oximeter probes may be used. The electronics and other peripheral components needed to receive and use information provided by the sensor form part of the overall system controller. In the preferred embodiment, a fluid catheter with oximeter wire attached extends between the shunt and an implantable enclosure which contains the oximeter circuits, battery, bladder pump, fluid reservoir and all other control electronics used to control the apparatus.

Additional features of the invention will become apparent and a fuller understanding obtained by reading the following detailed description made in connection with the accompanying drawings.

BEST MODE FOR CARRYING OUT THE INVENTION

Figure 1:
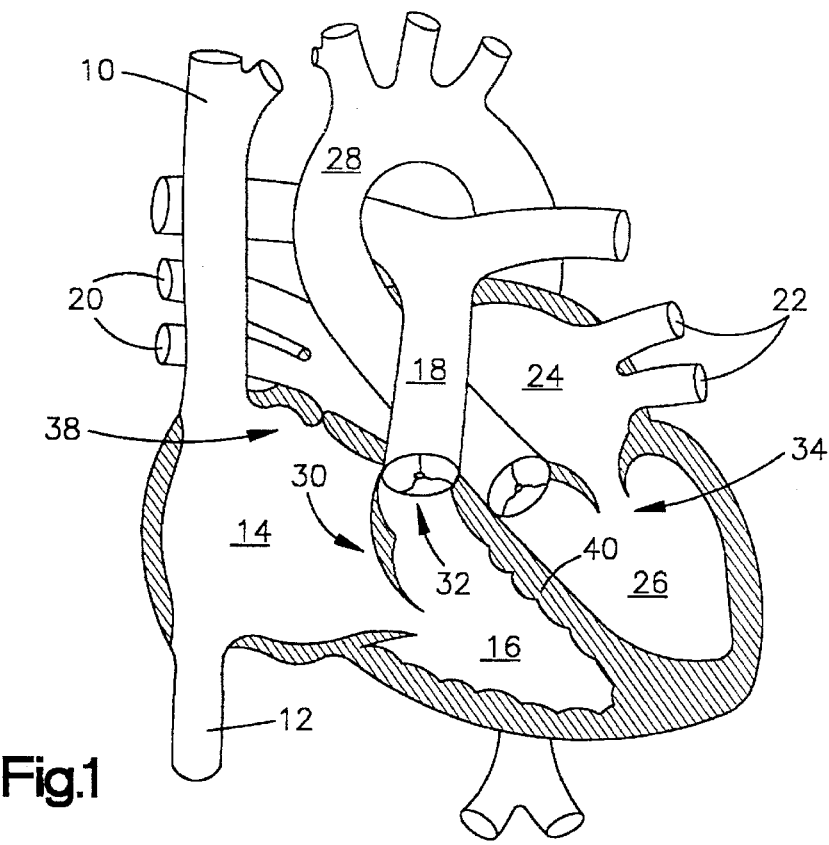
FIG. 1 illustrates a normal human heart.

FIG. 1 illustrates the physiology of a normal heart. As is known, blood flows from the body via large veins, termed the superior and inferior vena cavae 10, 12, respectively, to the right atrium 14. The blood received by the right atrium 14 is normally referred to as unoxygenated, but in reality has an oxygen content of 40%–70% and generally has a blue color cast. From the right atrium 14, the blood flows to the right ventricle 16 where it is pumped into the pulmonary artery 18. The pulmonary artery carries the unoxygenated blood to the lungs where it is oxygenated to 99% of capacity. The blood is then returned to the heart through the left and right pulmonary veins 20, 22. The blood enters the left atrium 24, and then the left ventricle 26 where it is pumped to the aorta 28. As is known, the aorta 28 is the main artery in the body and all arteries in the body are branches of the aorta.

Four valves within the heart keep blood flowing in the correct direction. A tricuspid valve 30 is between the right atrium 14 and right ventricle 16. A pulmonary valve 32 is between the right ventricle 16 and the pulmonary artery 18. A mitral valve 34 is between the left ventricle 26 and left atrium 24. An aortic valve 36 is between the left ventricle 26 and the aorta 28.

In a normal heart, blood does not flow between the right and left atria, because of a dividing wall 38 between the two chambers, which is termed the "interatrial septum". The interatrial septum does have a flap valve which allows blood to go from the right to the left atrium, if the pressure in the right atrium is abnormally high. In a normal situation, the pressure in the two atria are substantially the same.

A wall 40 between the ventricles 16, 26, is termed the "interventricular septum", prevents blood flow between the right and left ventricles. The pressure in the left ventricle which is the same as aorta pressure is usually higher than the pressure in the right ventricle (which communicates with the pulmonary artery), so if there is a hole in the interventricular septum (termed a ventricular septal defect), blood will flow from the left ventricle 26 (which is connected to the aorta 28) towards the right ventricle 16 (which is connected to the pulmonary artery 18). The resulting blood flow is in a direction that is opposite to standard blood flow.

Figure 2:
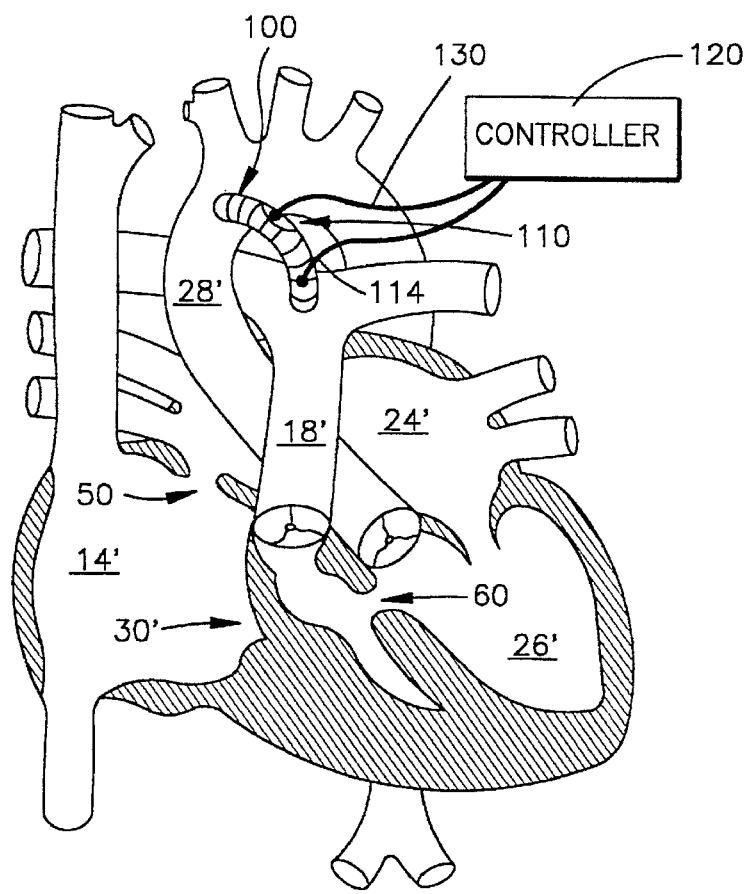
FIG. 2 illustrates an example of a human heart with a cyanotic congenital heart defect with the invention installed.

FIG. 2 illustrates an example of a heart defect to which the present invention is applicable. The heart defect disclosed in FIG. 2 is usually termed "tricuspid atresia" and is an example of cyanotic heart disease. A cyanotic heart disease is one in which there is too little blood flow to the lungs and, as a result, the blood leaving the heart is not sufficiently oxygenated. A patient having this disease will often exhibit a bluish hue.

When describing the physiology of the heart in FIG. 2, portions or elements of the heart shown in FIG. 2, which are substantially similar to portions and elements of the heart illustrated in FIG. 1, will be given the same reference character followed by an apostrophe.

In tricuspid atresia, the tricuspid valve 30' is "atretic" or absent. Referring to FIG. 2, with this defect, blood flows through an atrial septa defect indicated generally by the reference character 50, into the left atrium 24'.

From the left atrium, the blood enters the left ventricle 26'. In the defect illustrated in FIG. 2, which is a common defect associated with tricuspid atresia, blood flows from the left ventricle 26' to the pulmonary artery 18' through a ventricular septal defect 60. Since the ventricle septal defect is usually small, most blood flows directly to the aorta 28' and, as a result, a significant amount of blood has a low oxygen saturation. The percentage of blood that has a satisfactory saturation is dependent upon how much is able to flow through the ventricle septal defect 60 into the pulmonary artery. If a large percentage of blood makes it to the pulmonary artery, the patient will be well saturated with oxygen in his arteries. If little blood flow makes it to the pulmonary artery, from the left ventricle, the patient will have less oxygen in his arteries and will, thus, be cyanotic.

FIG. 2 illustrates one embodiment of the invention which may be used to treat the illustrated cyanotic congenital heart defect. According to the invention, a systemic-pulmonary shunt 100 is connected between the pulmonary artery 18' and the aorta 28'. The shunt itself may be a conventional shunt which consists of a prosthetic graft made from Gore-Tex® or other material. As is known, the shunt conveys blood from the aorta 28' to the pulmonary artery 18' where it then travels to the lungs (not shown) to be oxygenated. The level of oxygen saturation in the blood entering the aorta 28' is a function of the blood flow rate through the shunt 100, as well as the blood flow rate of blood flowing into the pulmonary artery 18' from other sources.

According to the invention, the shunt 100 includes an adjustable restrictor or valve, indicated generally by the reference character 110. In addition, a sensor 114 is attached to the shunt 100 and monitors the oxygen saturation of the blood flowing through the shunt. A controller 120 is preferably implanted in the patient and is connected to the restrictor 110 and the sensor 114.

Figure 3:
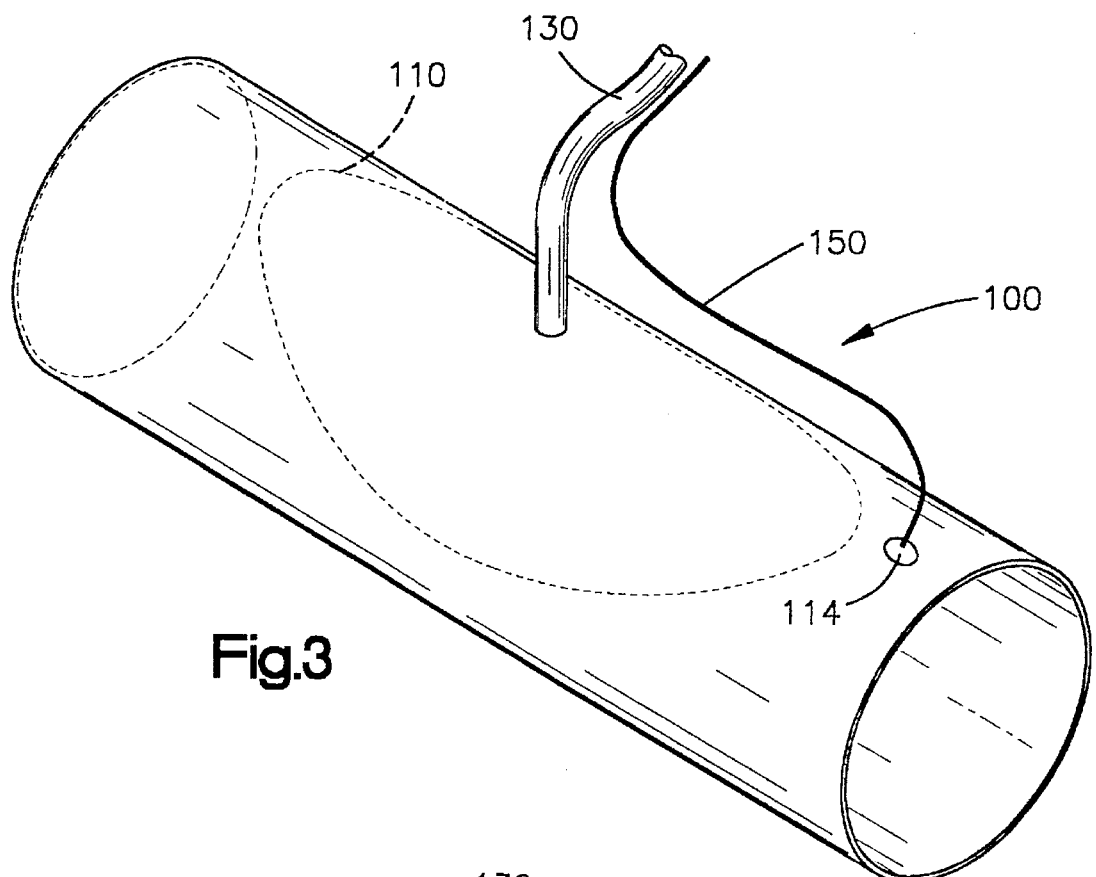
FIG. 3 illustrates a section of the systemic-pulmonary shunt showing one embodiment of the invention.
Figure 4:
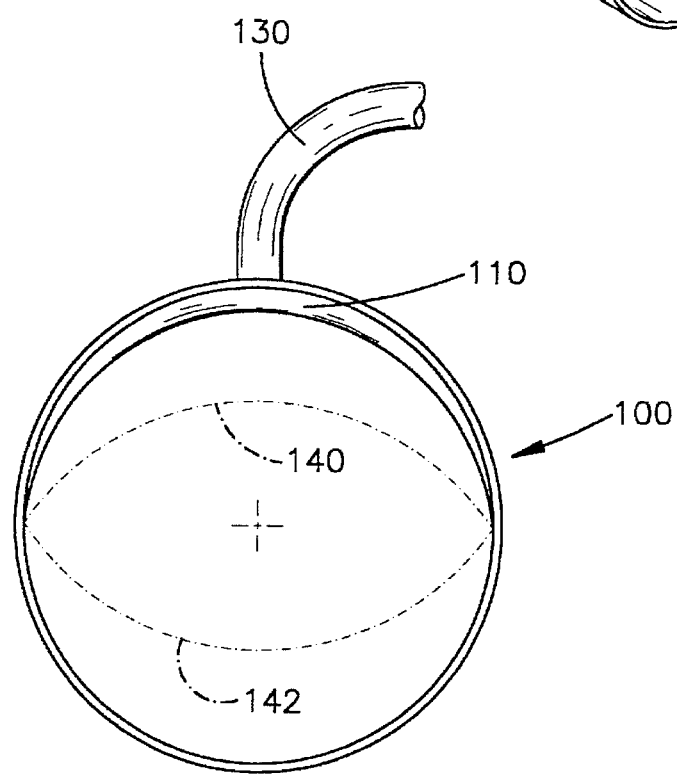
FIG. 4 is a sectional view of the shunt portion shown in FIG. 3.

Referring also to FIG. 3, in the preferred embodiment, the restrictor 110 comprises an inflatable bladder that is mounted to and/or forms part of the shunt 100. In the illustrated embodiment, the controller 120 includes a reservoir of bladder fluid (not shown) that may be pumped into the bladder through a supply tube 130. The bladder construction shown in FIGS. 3 and 4 is intended to serve as an example and those skilled in the art will recognize that other bladder constructions may be provided and, for that matter, other types of restrictors, such as motor driven valves, may be used.

In the illustrated embodiment, the bladder 110 is suitably attached to an inside wall of the shunt 100 and extends partially around the inner circumference. When fluid is pumped into the bladder as shown in FIG. 4, the bladder expands downwardly (as viewed in FIG. 4) to partially close-off or effectively reduce the cross-section of the shunt. The bladder should be made of blood-compatible material whose compliance is greater than that of the vascular graft material, so that the bladder bows into the lumen when inflated rather than pushing out the wall of the graft. Because the preferred length of the bladder is 8–10 mm in length, less reduction in cross-section is needed to provide a given reduction in flow than if a very thin resistor were used. In the preferred embodiment, the bladder does not present a sudden obstruction to flow, but rather provides a smooth transition to the restricted portion of the shunt. In this way, turbulent flow in the blood is not induced and damage to the blood is thus minimized. As seen in FIG. 3, when viewed in plan, the bladder appears oval in shape. When minimally inflated, the bladder preferably conforms to the inside wall of the shunt (shown in FIG. 4) and provides little restriction to the blood flow. A partially restricting position is indicated by the dashed line 140 in FIG. 4.

Preferably, the bladder and associated source of fluid for expanding the bladder, are configured such that when near-maximally inflated, the bladder does not fully close-off the fluid path. This is shown and indicated by the dashed line 142 in FIG. 4. The bladder itself may be formed from an integral balloon attached to the inside of the shunt 100 or, alternately, may be formed by a sheet of elastomeric material having a peripheral edge attached to the inside of the shunt.

It is known in the medical field that the inner lining of prosthetic grafts may develop pseudo-intima. Pseudo-intima is debris or other material carried by the blood that attaches itself to the inside lining of the graft, in this case the shunt 100. According to a feature of the invention, the bladder may be periodically inflated to a predetermined state in order to deal with the pseudo-intima phenomenon. By periodically expanding the bladder, it is believed that the formation of pseudo-intima in the shunt will be inhibited or dislodged. It is believed that in the preferred embodiment, the bladder should be periodically inflated to a condition greater than its normal maximum. The inflation would be of a short duration so that blood flow in the shunt is not substantially affected.

The fluid supply tube or catheter 130 extending between the bladder 110 and the controller 120 supplies and receives fluid from the bladder in order to adjust its relative size within the shunt. The sensor 114 for monitoring oxygen levels in the blood may take several forms. In one form the sensor may comprise a conventional oximeter. A signal line 150 extending from the sensor site on the shunt 100 may extend separately to the controller 120 or, preferably, may form part of a composite cable with the fluid catheter 130. The sensor 114 itself may pierce the shunt wall in order to have direct access with the blood or, alternately, if an optical sensor is used, the shunt may be provided with an optical window through which the sensor may be optically coupled to the blood.

The controller 120 is preferably implanted in a subcontaneous position and may use well known "pacemaker" technology in order to seal the internals of the controller from the body fluids. The controller housing may include a battery for supplying power to the controller, the fluid pump for the bladder and the oximeter. The controller housing may also include the fluid reservoir associated with the bladder, as well as the pump and pump motor for adding and removing fluid from the bladder. The controller may also include circuits for sending and receiving signals to provide a means for adjusting parameters, performing diagnostics, etc. on the controller by external equipment, as is common in "pacemaker" technology. For example, the controller may include a means for receiving control signals from devices outside the patient's body. The external devices may be utilized to send signals to the controller for manually adjusting the size of the restrictor in order to manually adjust the flow rate of blood through the shunt. This application of the invention would be utilized in those situations in which an oxygen sensor or oximeter is not used or is inoperative and, as a result, the restrictor must be manually adjusted by a treating physician or other personnel. The external devices may also be used to re-set or adjust the target setting for the oxygen saturation limits which the controller stores in order to determine when adjustments to the restrictor are needed. The technology for sending these control signals, without transgressing the skin of the patient, is known and is utilized, for example, by the pacemaker industry.

The technology for supplying fluid to the bladder in order to adjust the cross-section of the shunt may employ technology used in diabetic insulin pumps where the flow of small quantities of fluids are metered and controlled.

Although the invention has been described with a certain degree of particularity, it should be understood that various changes can be made to it without departing from the spirit of scope of the invention as hereinafter claimed. In particular, it is within the scope of this invention to have a shunt with a resistor but without an oximeter. The resistor, along with its pump, could be controlled with an external device rather than be controlled by an internally contained program. The information needed to employ appropriate changes in the resistor would be gained by the physician from clinical information provided by devices or equipment that do not form part of the invention.

I claim:

1. A method for treating a congenital heart defect, comprising the steps of:
   a) implanting a shunt within a patient's chest cavity for communicating arterial blood to a pulmonary artery;
   b) providing an adjustable flow restriction within said shunt for adjusting the blood flow rate in said shunt;
   c) adjusting said flow restriction to maintain the oxygen level in said blood within desired limits.

2. The method of claim 1 further comprising the step of monitoring the oxygen level of the blood flowing through said shunt using a sensor.

3. The method of claim 1 further comprising the step of providing an expandable bladder as part of said shunt and providing a fluid supply for filling said bladder in order to expand said bladder in the flow path defined by said shunt whereby a restriction to blood flow is provided depending on the extent to which said bladder is expanded.

4. The method of claim 2, wherein said step of monitoring the oxygen level of the blood flowing through said shunt is provided by an oximeter having a sensing probe attached to said shunt.

5. The method of claim 3, further comprising the step of periodically expanding said bladder to a predetermined state in order to inhibit the formation of pseudo-intima.

6. An apparatus for treating congenital heart defects, comprising:
   a) a systemic-pulmonary shunt implanted within a patient's chest cavity having one end adapted to be attached to the patient's arterial system and another end adapted to be attached to the patient's pulmonary system and operative to communicate blood from the patient's arterial system to the patient's pulmonary system;
   b) an adjustable flow restrictor forming part of said shunt, said adjustable flow restrictor having at least three effective sizes;
   c) an oximeter including a probe in communication with blood flowing in said shunt;
   d) a restrictor control system responsive to said oximeter to vary the effective size of said flow restrictor, said effective size of said flow restrictor being a function of the oxygen saturation level in the blood whereby a blood flow rate through said shunt is adjusted to maintain a oxygen saturation level in said blood between predetermined limits, one limit being substantially 40% and the other limit being substantially 99%; and,
   e) an implantable power source for providing power for said control system.

7. The apparatus of claim 6, wherein said adjustable flow restrictor comprises an inflatable bladder.

8. The apparatus of claim 7, wherein said bladder is constructed of a blood compatible material having a compliance that is greater than that of a material from which the shunt is constructed.

9. The apparatus of claim 6, wherein said adjustable flow restrictor comprises a bladder formed by a sheet of elastomeric material, a periphery of said bladder material being fastened to an inside portion of said shunt.

10. The apparatus of claim 7, wherein said restrictor control includes a pump and a reservoir of fluid, the fluid in said reservoir being communicated to and from said bladder by said pump in order to inflate said bladder thereby reducing an effective cross-section of said shunt.

11. The apparatus of claim 10, wherein said pump is controlled by said restrictor control system and is operative to fill and deflate said bladder in response to sensed oxygen saturation levels in the blood stream.

12. The apparatus of claim 11, further comprising a means for expanding said bladder periodically in order to inhibit or dislodge the formation of pseudo-intima.

13. The apparatus of claim 11, wherein said controller stores target values for said oxygen saturation levels and which are compared with said sensed oxygen saturation levels in order to determine whether an inflation state of said bladder needs to be adjusted.

14. The apparatus of claim 13, further comprising external devices for sending signals to said restrictor control system in order to change said stored target saturation levels.

15. An apparatus for treating congenital heart defects, comprising:
   a) a systemic-pulmonary shunt implanted within a patient's chest cavity having one end adapted to be attached to the patient's arterial system and another end adapted to be attached to the patient's pulmonary system and operative to communicate blood from the patient's arterial system to the patient's pulmonary system;
   b) an adjustable flow restrictor forming part of said shunt, said adjustable flow restrictor having at least three effective sized;
   c) an oxygen sensor in communication with blood flowing in said patient;
   d) a restrictor control system responsive to said sensor to vary the effective size of said flow restrictor whereby a blood flow rate in said shunt is adjusted to maintain an oxygen saturation level in said blood between predetermined limits, one limit being substantially 40% and the other limit being substantially 99%; and,
   e) an implantable power source for providing power for said control system.

16. The apparatus of claim 15, wherein said oxygen sensor comprising an oximeter.

17. The apparatus of claim 15, wherein said adjustable flow restrictor comprises an inflatable bladder for adjusting the effective size of said restrictor.

18. An apparatus for treating congenital heart defects, comprising:
   a) a systemic-pulmonary shunt implanted within a patient's chest cavity having one end adapted to be attached to the patient's arterial system and another end adapted to be attached to the patient's pulmonary system and operative to communicate blood from the patient's arterial system to the patient's pulmonary system;
   b) an adjustable flow restrictor forming part of said shunt, said adjustable flow restrictor having at least three effective sizes;
   c) a restrictor control system operative to vary the effective size of said flow restrictor whereby a blood flow rate in said shunt is adjusted to maintain a oxygen saturation level in said blood between predetermined limits, one limit being substantially 40% and the other limit being substantially 99%; and,
   d) an implantable power source for providing power to said control system.

19. The apparatus of claim 18, further comprising an oxygen sensor for monitoring the oxygen saturation level in the patient's blood.

20. The apparatus of claim 19, wherein said restrictor control system is responsive to oxygen saturation levels sensed by said sensor.

21. The apparatus of claim 19, wherein said oxygen sensor comprises an oximeter.

22. The apparatus of claim 21, wherein said oximeter directly monitors the oxygen saturation level of blood flowing in said shunt.

23. The apparatus of claim 18, further comprising a means for receiving control signals from a device external to the patient's chest, said restrictor control system responding to said control signals to change the effective size of said flow restrictor.

24. The apparatus of claim 18, wherein said predetermined limits of the oxygen saturation level are stored within said restrictor control system.

25. The apparatus of claim 24, wherein said predetermined limits are changeable by control signals issued by a device external to said patient's chest.

26. An apparatus for treating congenital heart defects, comprising:
   a) a shunt implanted within a patient's chest cavity for communicating blood from the patient's arterial system to the patient's pulmonary system;
   b) an adjustable flow restrictor forming part of said shunt;
   c) a restrictor control system operative to vary an effective size of said flow restrictor whereby a blood flow rate in said shunt is adjusted to maintain a oxygen saturation level in said blood between predetermined limits;
   d) an oxygen sensor for monitoring the oxygen saturation level in the patient's blood, said oxygen sensor comprising an oximeter that directly monitors the oxygen saturation level of blood flowing in said shunt; and,
   e) an implantable power source for providing power to said control system.

27. For a patient having a first vascular structure and a second vascular which under normal conditions receives blood that has travelled through the first vascular structure, an apparatus for treating congenital heart defects, comprising:
   a) a shunt implanted within a patient's chest cavity having one end adapted to be attached to the first vascular structure of the patient and another end adapted to be attached to the second vascular structure of the patient and operative to communicate blood from the patient's second vascular structure to the patient's first vascular structure;
   b) an adjustable flow restrictor forming part of said shunt, said adjustable flow restrictor having at least three effective sizes;
   c) an oximeter including a sensor for monitoring the oxygen level of blood flowing through the patient;
   d) a restrictor control system responsive to said oximeter to vary the effective size of said flow restrictor said effective size of said flow restrictor being a function of the oxygen saturation level in the blood whereby a blood flow rate through said shunt is adjusted to maintain a oxygen saturation level in said blood between predetermined limits, one limit being substantially 40% and the other limit being substantially 99%; and,
   e) an implantable power source for providing power for said control system.

* * * * *